United States Patent [19]

Schleppnik et al.

[11] 4,009,253
[45] Feb. 22, 1977

[54] 4-CYCLOHEXYL-4-METHYL-2-PENTANONE USEFUL AS A MALODOR COUNTERACTANT

[75] Inventors: Alfred A. Schleppnik, St. Louis, Mo.; Steve G. Vanata, Midland Park, N.J.

[73] Assignee: Monsanto Company, St. Louis, Mo.

[22] Filed: Mar. 17, 1975

[21] Appl. No.: 558,574

Related U.S. Application Data

[63] Continuation of Ser. No. 413,082, Nov. 5, 1973, abandoned.

[52] U.S. Cl. .................................. 424/45; 8/161; 424/65; 424/76; 424/331
[51] Int. Cl.² ................ A61L 9/04; A61L 13/00
[58] Field of Search ................. 424/45, 331, 76

[56] References Cited
FOREIGN PATENTS OR APPLICATIONS
300,113   9/1965   Netherlands

OTHER PUBLICATIONS

Byers, Chem. Abst., vol. 41, 4614 (1947).

*Primary Examiner*—Albert T. Meyers
*Assistant Examiner*—Allen J. Robinson
*Attorney, Agent, or Firm*—Howard C. Stanley

[57] ABSTRACT

Compositions and methods for counteracting malodors. 4-cyclohexyl-4-methyl-2-pentanone has been found to be particularly useful in such compositions and methods.

4 Claims, No Drawings

4-CYCLOHEXYL-4-METHYL-2-PENTANONE USEFUL AS A MALODOR COUNTERACTANT

CROSS-REFERENCES TO RELATED APPLICATIONS

This is a continuation of application Ser. No. 413,082, filed Nov. 5, 1973, now abandoned.

FIELD OF THE INVENTION

This invention relates to the art of treatment of offensive odors, more particularly, to compositions and methods to counteract certain malodors.

DESCRIPTION OF THE PRIOR ART

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than the natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Such needs vary over a very wide spectrum. Accordingly, there is a great need in the art of fragrance compositions for compounds possessing specific olfactory characteristics.

Heretofore a major effort in the art of perfumery has been directed to providing means of treating odors that are offensive to the human sense of smell. Such odors encompass a variety of odors such as bathroom-odor, kitchen-odor, body-odor, cigar smoke-odor, etc. Many products have been developed in an attempt to overcome these odors. So-called "room fresheners" or "deodorants" are illustrative of such products.

In general these products provide a masking effect by one of two mechanisms. The maskant fragrance is provided either to suppress the offensive odor by providing a more pleasing aroma in large quantities or by providing an aroma that blends with the offensive odor to provide a different and more desirable aroma. Unfortunately, in both instances a large amount of fragrance must be utilized which in itself often proves to be offensive. Furthermore, the offensive odor is usually still detectable at the levels of maskant fragrances that are reasonably tolerable. Accordingly, compositions and methods for counteracting such offensive odors which would substantially eliminate such odors without the above noted disadvantages are particularly desirable.

Particularly noxious odors are caused by compounds which have a pronounced tendency to either donate or accept protons. Such compounds will hereinafter be referred to as "malodors". They include the olfactory notorious classes of lower carboxylic acids, thiols, thiophenols, phenols, lower amines, phosphines and arsines.

SUMMARY OF THE INVENTION

The present invention provides novel compositions which are especially useful in view of their ability to counteract malodors. Furthermore, novel methods are provided, i.e. the use of such novel compositions to counteract malodors.

The instant substance which exhibits this surprising ability to counteract malodors is 4-cyclohexyl-4-methyl-2-pentanone (hereinafter referred to as "CMP").

DESCRIPTION OF THE PREFERRED EMBODIMENTS

The term "counteract" as used herein means the effect on the human sense of smell and/or the malodor resulting in alleviating the offensiveness of the malodor to the human sense of smell. It is not intended that this term be limited to any particular mechanism by which such a result may be obtained.

Surprisingly CMP is capable of effectively counteracting malodors when utilized in small quantities. CMP can be used in many different mediums to counteract malodors. For instance, use in room fresheners or deodorants in the form of aerosols (sprays, etc.), liquids (wick type), solids (wax bases as in pomander, plastics, etc.), powders (sachets, dry sprays) and gels (solid gel sticks) are particularly preferred. Other illustrative uses are in clothes deodorants as applied by washing machine applications such as in detergents, powders, liquids, whiteners or fabric softeners or by other applications such as closet blocks, closet aerosol sprays, or clothes storage areas or in dry cleaning to overcome residual solvent notes on clothes; in cleansers such as disinfectants and toilet bowl cleaners; in bathroom accessories such as paper towels, bathroom tissues, sanitary napkins, towellets, disposable wash clothes, disposable diapers, and diaper pail deodorants; in cosmetic products such as antiperspirant and underarm deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams, lotions, etc., medicated hair care products containing such ingredients as S-Selenium-sulfide, coal tar, salicylates, etc., or shampoos, or foot care products such as foot powders, liquids, or colognes, after shaves and body lotions, or soaps and synthetic detergents such as bars, liquids, foams, or powders; in odor control such as during manufacturing processes, such as in the textile finishing industry and the printing industry (inks and paper); in effluent control such as in processes involved in pulping, stock yard and meat processing, sewage treatment, or garbage disposal, or in product odor control as in textile finished goods, rubber finished goods, car fresheners, etc.; in agricultural and pet care products such as dog and hen house effluents, and domestic animal and pet care products such as deodorants, shampoo or cleaning agents, or animal litter materials; in large scale closed air systems such as auditoriums, and subways and transport systems.

The amount of CMP to be utilized depends, in general, on the particular malodor involved and its concentration and on other variables such as the medium in which it is used and the temperature, humidity and air circulation. An effective amount should be used. In general, CMP is effective when present in the air (in which the maloder is located) at a level as low as about 0.01 mg./cubic meter of air. Any concentration above this amount will generally be effective. However, from a practical point of view, more than about 1 mg./cubic meter of air is probably unnecessary with even the most offensive and concentrated malodors.

CMP can be prepared by reacting benzene with mesityl oxide to form 4-methyl-4-phenyl-2-pentanone which is then subjected to appropriate hydrogenation.

The following examples are given to illustrate the instant invention in detail. It is to be understood that the specific details given in the examples are not to be construed as limiting the scope of the invention. The symbol "mg./cu. meter" refers to the weight (in milligrams) of material present in one cubic meter of air.

EXAMPLE 1

The following malodor concentrates were prepared:

Burned Tobacco Malodor Concentrate

| Component | Parts by Wt. |
| --- | --- |
| furfural | 5.0 |
| pyridine | 0.1 |
| methyl ethyl pyridine | 12.6 |
| 95% aqueous solution of thioglycolic acid | 0.7 |
| Beechwood cresote | 1.2 |
| pyroligneous acid | 30.6 |
| dipropylene glycol | 49.8 |

Body Malodor Concentrate

| Component | Parts by Wt. |
| --- | --- |
| n-caproic acid | 30.00 |
| isovaleraldehyde | 30.00 |
| phenylacetic acid | 3.00 |
| butyric acid | 0.25 |
| indole (0.5% solution in dipropylene glycol) | 1.50 |
| para-cresyl isovalerate | 1.50 |
| para-cresyl phenyl acetate | 2.75 |
| 95% aqueous solution of thioglycolic acid | 5.00 |
| dipropylene glycol | 26.00 |

Bathroom Malodor Concentrate

| Component | Parts by Wt. |
| --- | --- |
| skatole | 0.91 |
| -thionaphthol | 0.91 |
| 95% aqueous solution of thioglycolic acid | 21.18 |
| n-caproic acid | 6.00 |
| p-cresyl isovalerate | 2.18 |
| N-methyl morpholine | 6.00 |
| dipropylene glycol | 62.82 |

Aerosol cans were prepared with each of the above malodors with the following concentrations:

Burned Tobacco Malodor Aerosol

| Component | Parts by Wt. |
| --- | --- |
| Burned Tobacco Malodor Concentrate | 0.2 |
| dipropylene glycol | 4.8 |
| Freon propellant -F 11/12 (50/50)* | 95.0 |

Body Malodor Aerosol

| Component | Parts by Wt. |
| --- | --- |
| Body Malodor Concentrate | 0.1 |
| dipropylene glycol | 4.9 |
| Freon propellant -F 11/12 (50/50) | 95.0 |

Bathroom Malodor Aerosol

| Component | Parts by Wt. |
| --- | --- |
| Bathroom Malodor Concentrate | 0.1 |
| dipropylene glycol | 4.9 |
| Freon propellant -F 11/12 (50/50) | 95.0 |

Four fragrance compositions were prepared, each containing 10% by weight of CMP. These are identified, based on the fragrance effect, as:

Fragrance

Floral bouquet
Cologne spice
Lavender bouquet
Ozone type

Aerosol cans were prepared with each of the above fragrance compositions with the fragrance composition being present in a concentration of 0.5% with Freon Propellant -F 11/12 (50/50) constituting the remaining material in the system.

A test chamber having inside dimensions of 11' × 12' × 8' with a total volume of 29.9 cubic meters, having an access door which refers to a mixture containing 50 percent, by weight, trichloro monofluoro methane (Freon-11) and 50 percent, by weight, dichloro difluoro methane (Freon-12) which are Trademarks of the E. I. duPont deNemours and Company, Wilmington, Delaware. and an exhaust fan was provided. The capacity of the exhaust fan was 800 cu. feet/min. In order to insure satisfactory evacuation the exhaust fan was operated for five minutes between tests and an olfactory check was made to determine if any residual odor could be detected prior to conducting the next test.

After the test chamber had been suitably evacuated the malodor to be utilized was sprayed from the aerosol can for about five seconds. After a delay of from 10–15 seconds the fragrance composition aerosol was sprayed for about five seconds (five seconds being an average time such an aerosol would usually be used by a housewife). One minute thereafter a 10 member panel (consisting of 7 persons skilled in perfumery and odor evaluation and 3 persons having no such special skills but being familiar with fragrances in general) entered the test chamber, performed an olfactory evaluation for detection of the malodor and recorded their observations. All tests were performed with only one (1) member of the panel being aware of the identity of the material being tested.

Based on flow rates through the valves utilized in the aerosol cans the approximate amounts of aerosol containing the malodor concentrate introduced into the test chamber are:

| Aerosol Containing Malodor Concentrate | Amount (mg./cu.meter) |
| --- | --- |
| Burned Tobacco | 267 |

| Aerosol Containing Malodor Concentrate | Amount (mg./cu.meter) |
|---|---|
| Body | 168 |
| Bathroom | 267 |

The amount of aerosol containing the fragrance compositions introduced into the test chamber is approximately 260 mg./cu. meter.

When the above described test procedure was carried out using each of the fragrance composition aerosols containing CMP (tested against each of the three above-mentioned malodors) at least eight (8) members of the panel could not detect the presence of the malodors. These are particularly surprising results because when the floral bouquet fragrance composition aerosol not containing CMP is tested at least six (6) members of the panel detected the presence of the malodors.

EXAMPLE 2

Four well known commercial products were also utilized in the above-described test procedures against each of the above described malodors. (Amounts utilized based on 5 second spray);

| Commercial Product | Amount (mg./cu.meter) |
|---|---|
| A | 152 |
| B | 170 |
| C | 150 |
| D | 68 |

With all of these commercial products at least six (6) members of the panel detected the presence of the malodors.

EXAMPLE 3

An aerosol can was prepared with the following concentrations:

| Component | Parts by Wt. |
|---|---|
| CMP | 0.05 |
| Freon propellant -F 11/12 (50/50) | 99.95 |

The aerosol was utilized in the above-described test procedures against each of the above-described malodors (aerosol 267 mg./cu. meter). At least eight (8) members of the panel could not detect the presence of the malodors.

This ability of CMP to counteract malodors is particularly surprising in view of the fact that a closely related compound, 4-cyclohexyl-3-methyl-2-pentanone, has little or no such ability.

While the invention has been described herein with regard to certain specific embodiments, it is not so limited. It is to be understood that variations and modifications thereof may be made by those skilled in the art without departing from the spirit and scope of the invention.

The embodiments of this invention in which an exclusive property or privilege is claimed are defined as follows:

1. A method of treating malodors to alleviate their offensive odors which comprises treating the air containing the malodor with an amount of 4-cyclohexyl-4-methyl-2-pentanone which is effective to counteract the malodor.

2. The method according to claim 1 wherein the 4cyclohexyl-4-methyl-2-pentanone is provided in an amount sufficient to provide at least 0.01 mg./cubic meter of air in the environment containing the malodor.

3. The method according to claim 1 wherein 4-cyclohexyl-4-methyl-2-pentanone is utilized in the form of a room freshener.

4. The method according to claim 3 wherein the room freshener is introduced as an aerosol.

* * * * *

UNITED STATES PATENT OFFICE
CERTIFICATE OF CORRECTION

PATENT NO. : 4,009,253
DATED : February 22, 1977
INVENTOR(S) : Alfred A. Schleppnik and Steve G. Vanata It is certified that error appears in the above-identified patent and that said Letters Patent are hereby corrected as shown below:

Column 3, line 50, before "-thionaphthol" there should be inserted -- β --; same column, as a footnote after "Burned Tobacco Malodor Aerosol Table" there should be added -- *which refers to a mixture containing 50 percent, by weight, trichloromonofluoro methane (Freon-11) and 50 percent, by weight, dichlorodifluoro methane (Freon-12) which are Trademarks of the E. I. duPont deNemours and Company, Wilmington, Delaware. --

Column 4, line 33, after "door" through line 38, there should be deleted up to the word "Delaware,"; same column, line 39, "800" should be corrected to read -- 500 --.

Column 5, line 5, "168" should be corrected to read -- 166 --.

Signed and Sealed this

Fourteenth Day of June 1977

[SEAL]

Attest:

RUTH C. MASON
Attesting Officer

C. MARSHALL DANN
Commissioner of Patents and Trademarks